US011697630B2

(12) United States Patent
Andrade et al.

(10) Patent No.: US 11,697,630 B2
(45) Date of Patent: Jul. 11, 2023

(54) HIGH-GRADE ETHANOL PRODUCTION PROCESS

(71) Applicant: WHITEFOX TECHNOLOGIES LIMITED, London (GB)

(72) Inventors: Virginia Andrade, Calgary (CA); Stephan Blum, Calgary (CA); Thiago Righi, Calgary (CA); Zhou Jin Ming, Calgary (CA)

(73) Assignee: WHITEFOX TECHNOLOGIES LIMITED, London (GB)

( * ) Notice: Subject to any disclaimer, the term of this patent is extended or adjusted under 35 U.S.C. 154(b) by 0 days.

(21) Appl. No.: 17/398,702

(22) Filed: Aug. 10, 2021

(65) Prior Publication Data

US 2022/0048841 A1     Feb. 17, 2022

Related U.S. Application Data

(60) Provisional application No. 63/121,442, filed on Dec. 4, 2020, provisional application No. 63/064,110, filed on Aug. 11, 2020.

(51) Int. Cl.
*B01D 3/00*     (2006.01)
*B01D 3/14*     (2006.01)
(Continued)

(52) U.S. Cl.
CPC ............. *C07C 29/84* (2013.01); *B01D 3/002* (2013.01); *B01D 3/145* (2013.01); *B01D 3/148* (2013.01);
(Continued)

(58) Field of Classification Search
CPC .... C12H 6/00; C12H 6/02; B01D 3/001–005; B01D 3/145; C12F 3/04; C12F 3/06;
(Continued)

(56) References Cited

U.S. PATENT DOCUMENTS 4,217,178 A *   8/1980   Katzen ................... B01D 3/005
                                                                                                                   203/69
4,422,903 A *   12/1983   Messick ................. B01D 3/065
                                                                                                                    203/25
(Continued)

FOREIGN PATENT DOCUMENTS

WO      WO 2012/006388        1/2012
WO      WO-2014097311 A1 *   6/2014           B01D 3/002

OTHER PUBLICATIONS

Eniko Haaz, Daniel Fozer, and Andras Jozsef Toth, "Development of Anhydrous Ethanol Purification: Reduction of Acetal Content and Vapor-Liquid Equilibrium Study of the Ethanol-Acetal Binary System", ACS Omega 2021 6 (2), 1289-1298, DOI: 10.1021/acsomega. 0c04750.*

(Continued)

*Primary Examiner* — Jonathan Luke Pilcher
(74) *Attorney, Agent, or Firm* — K&L Gates LLP

(57) ABSTRACT

The present disclosure provides high-grade ethanol production systems and methods that increase energy efficiency as compared to typical systems and methods by minimizing undesired acetal formation. The provided ethanol production method may include a low boilers removal distillation column and/or a stripper column constructed to simultaneously remove at least a portion of the acetaldehyde and at least a portion of the acetal from a feed stream in the presence of water. In some aspects, a low boilers removal process may be followed by a water removal process, which may be followed by a high boilers removal process. Acidity (e.g., carbon dioxide) may also be removed from a feed stream prior to or during the low boilers removal process. By minimizing acetal production, the provided method minimizes the amount of energy that is required to remove acetal when producing high-grade ethanol.

15 Claims, 11 Drawing Sheets

(51) Int. Cl.
 *C07C 29/84*  (2006.01)
 *C12H 6/02*  (2019.01)
 *C07C 29/76*  (2006.01)
 *C07C 29/80*  (2006.01)

(52) U.S. Cl.
 CPC .............. *C07C 29/76* (2013.01); *C07C 29/80* (2013.01); *C12H 6/02* (2019.02)

(58) Field of Classification Search
 CPC ... C12F 3/08; C12F 3/10; C07C 29/80; C07C 29/82; C07C 29/84
 See application file for complete search history.

(56) References Cited

U.S. PATENT DOCUMENTS

| | | | |
|---|---|---|---|
| 8,128,826 B2* | 3/2012 | Plante | C07C 29/76 95/52 |
| 8,877,987 B2* | 11/2014 | Johnston | C07C 29/149 568/885 |
| 9,000,233 B2* | 4/2015 | Lee | C07C 29/149 568/918 |
| 2008/0207959 A1* | 8/2008 | Plante | B01D 3/14 568/916 |
| 2008/0210540 A1 | 9/2008 | Dieterle | |
| 2009/0301970 A1* | 12/2009 | Noel | B01D 3/145 210/640 |
| 2012/0277493 A1* | 11/2012 | Lee | C07C 29/88 568/885 |
| 2013/0035525 A1* | 2/2013 | Johnston | C07C 29/84 568/885 |
| 2015/0224420 A1* | 8/2015 | Hickey | B01D 3/143 203/41 |

OTHER PUBLICATIONS

Search Report and Written Opinion dated Dec. 8, 2021 issued for International PCT Patent Application No. PCT/EP2021/072369 filed Aug. 11, 2021.

* cited by examiner

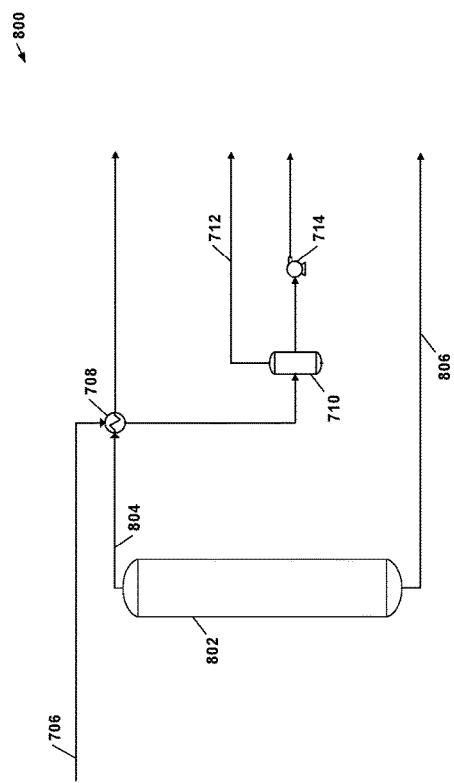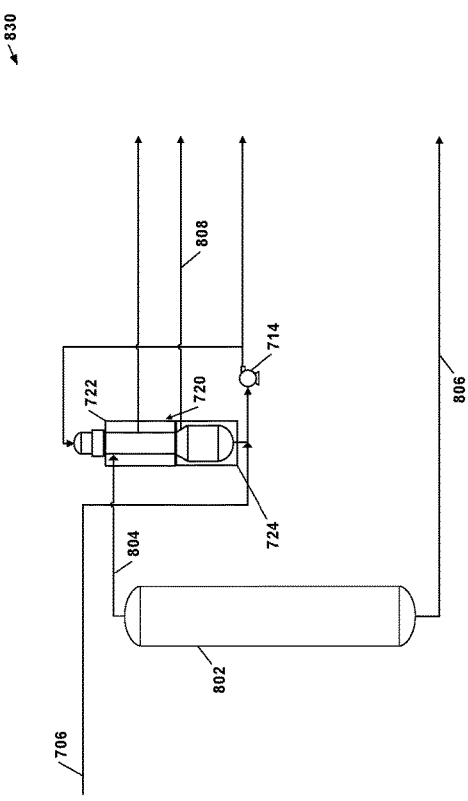
FIGURE 8A
FIGURE 8B

HIGH-GRADE ETHANOL PRODUCTION PROCESS

PRIORITY CLAIM

The present application claims priority to and the benefit of U.S. Provisional Application 63/064,110, filed Aug. 11, 2020, and U.S. Provisional Application 63/121,442, filed Dec. 4, 2020. The entirety of each are herein incorporated by reference.

BACKGROUND

To produce high-grade ethanol almost all trace components contained in the ethanol from fermentation (e.g., congeners) must be removed. For instance, the U.S. Pharmacopeia grade specifications for high-grade ethanol include 99.2 wt % ethanol, less than 200 ppm methanol, less than 10 ppm acetaldehyde and acetal combined, and less than 300 ppm of other organics (e.g., ethyl acetate and fusels). The trace components include carbon dioxide, water, low boiling components including methanol, acetaldehyde and ethyl acetate, and high boiling components including acetals and fusels (e.g., C3, C4, and C5 alcohols). To remove such trace components, a high-grade ethanol production process must include (1) a water removal step, (2) a low boiler component removal step, and (3) a high boiler component removal step.

One typical high-grade ethanol production process includes a water removal step followed by a low boilers removal step followed by a high boilers removal step. Such processes, however, are energy intensive. For instance, such processes include the use of up to six distillation columns. Additionally, such processes remove water in the first step through rectification to get the ethanol concentration to around 95%, and then remove the low boiling components in the second step through extractive distillation by adding significant amounts of water, thus diluting the ethanol back to about 15%. Then, the high boiling components are removed in the third step to increase the ethanol concentration again.

Another typical high-grade ethanol production process includes a water removal step followed by a high boilers removal step followed by a low boilers removal step. Such processes, however, are also energy intensive. For instance, the low boiling and high boiling components in such processes are typically removed through a combination of distillation columns after the ethanol is dehydrated through different separation methods, such as molecular sieves. This means that the low boiling and high boiling components are removed from anhydrous ethanol, which generates a significant disadvantage. Acetaldehyde and ethanol in the presence of an acid (i.e., carbon dioxide) form acetals and water according to the below reaction.

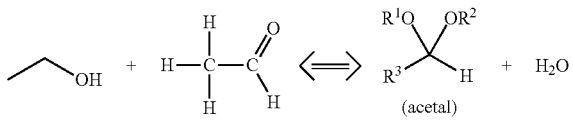

The above is an equilibrium reaction meaning that all components are present in some concentration. During dehydration, water is continuously removed which pushes the equilibrium to the right side of the reaction, continuously producing acetal. In high-grade ethanol production the acetal is typically diethoxyethane. Acetal is difficult to remove and it is therefore energy intensive to do so. Accordingly, the more acetal that is generated, the more energy that is required to remove acetal when producing the final high-grade ethanol. Further, the concentration of acetal cannot be above a certain threshold (e.g., 10 ppm) in the final high-grade ethanol. In some instances, the amount of acetal generated may be too great, so that it is not possible with typical ethanol production processes to remove enough acetal to produce high-grade ethanol without losing yield or conversion.

In addition, some typical processes add chemicals to avoid or reverse the formation of acetal, such as alkaline agents, e.g. sodium hydroxide, potassium hydroxide, calcium hydroxide, sodium borohydride or equivalent. The addition of chemicals increases the operational costs, can negatively impact product quality, and potentially introduces uncertified components to the final product.

Accordingly, a need exists for a high-grade ethanol production process that solves the above drawbacks.

SUMMARY

The present disclosure provides new and innovative systems and methods for high-grade ethanol production with increased energy efficiency as compared to typical high-grade ethanol production systems and methods. In various embodiments, the increased energy efficiency is achieved at least in part by a particular order of the processes in the provided high-grade ethanol production method, which includes low boilers removal prior to water removal, which is prior to high boilers removal. In some embodiments, the increased energy efficiency may be achieved at least in part by a low boilers removal distillation column and/or a stripper column constructed to simultaneously remove at least a portion of the acetaldehyde and at least a portion of the acetal from a feed stream in the presence of water, which enables rearranging the order of the processes in the provided method. For instance, the inventors have found that the thermodynamics of boiling a polynary azeotrope in the presence of water surprisingly enables removing significant amounts of acetal (boiling point of 102° C.) together with acetaldehyde (boiling point of 20° C.) via an overhead stream of a distillation or stripper column.

In an example, an ethanol production method includes a low boilers removal process, a water removal process, and a high boilers removal process. The low boilers removal process includes receiving at a first distillation column, a first feed stream including ethanol, low boiling components, high boiling components, and water; removing at least a portion of the low boiling components from the first feed stream via an overhead stream of the first distillation column; and producing a first bottom stream from the first distillation column. The water removal process includes receiving a second feed stream including ethanol, high boiling components, and water, the second feed stream including at least a portion of the first bottom stream; and removing at least a portion of the water from the second feed stream to produce an anhydrous stream. And the high boilers removal process includes receiving in a second distillation column, a third feed stream including ethanol and high boiling components, the third feed stream being at least a portion of the anhydrous stream; removing at least a portion of the high boiling components of the third feed stream from the third feed stream via a bottom stream of the second distillation column; and producing an overhead stream from the second distillation column. The overhead stream of the second distillation column includes a high-grade ethanol product.

In another example, an ethanol production method includes a low boilers removal process, a water removal process, and a high boilers removal process. The low boilers removal process includes receiving at a stripper column at least one feed stream including ethanol, low boiling components, high boiling components, and water; and removing at least a portion of the low boiling components from the at least one feed stream via an overhead stream of the stripper column. The water removal process includes generating a vaporous stream from the at least one feed stream via the stripper column; and removing at least a portion of the water from the vaporous stream via one or more membranes to produce an anhydrous stream including ethanol and high boiling components. And the high boilers removal process includes receiving the anhydrous feed stream; removing at least a portion of the high boiling components of the anhydrous feed stream from the anhydrous feed stream via a bottom stream of a distillation column; and producing an overhead stream from the distillation column. The overhead stream includes a high-grade ethanol product.

In another example, an ethanol production system includes a low boilers removal subsystem, a water removal subsystem in fluid communication with the low boilers removal subsystem, and a high boilers removal subsystem in fluid communication with the water removal subsystem. The low boilers removal subsystem includes a low boilers removal (LBR) distillation column constructed to receive a first feed stream, remove at least a portion of the low boiling components from the first received feed stream via an LBR distillation column overhead stream, and produce an LBR distillation column bottom stream. The first feed stream includes ethanol, low boiling components, high boiling components, and water. The water removal subsystem is constructed to receive a second feed stream, and remove at least a portion of the water from the second feed stream to produce an anhydrous stream. The second feed stream includes at least a portion of the first bottom stream. And the high boilers removal subsystem includes a high boilers removal (HBR) distillation column constructed to receive a third feed stream, remove at least a portion of the high boiling components of the anhydrous stream from the anhydrous stream via a bottom stream of the HBR distillation column, and produce an HBR distillation column overhead stream that includes a high-grade ethanol product. The third feed stream includes at least a portion of the anhydrous stream.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

BRIEF DESCRIPTION OF THE DRAWINGS

FIG. 8A illustrates a subsystem in which an overhead stream from a high boilers removal (HBR) distillation column exchanges heat with steam condensate, according to an aspect of the present disclosure.

FIG. 8B illustrates a subsystem in which an overhead stream from a high boilers removal (HBR) distillation column exchanges heat with steam condensate, according to an aspect of the present disclosure.

DETAILED DESCRIPTION

Figure 1:
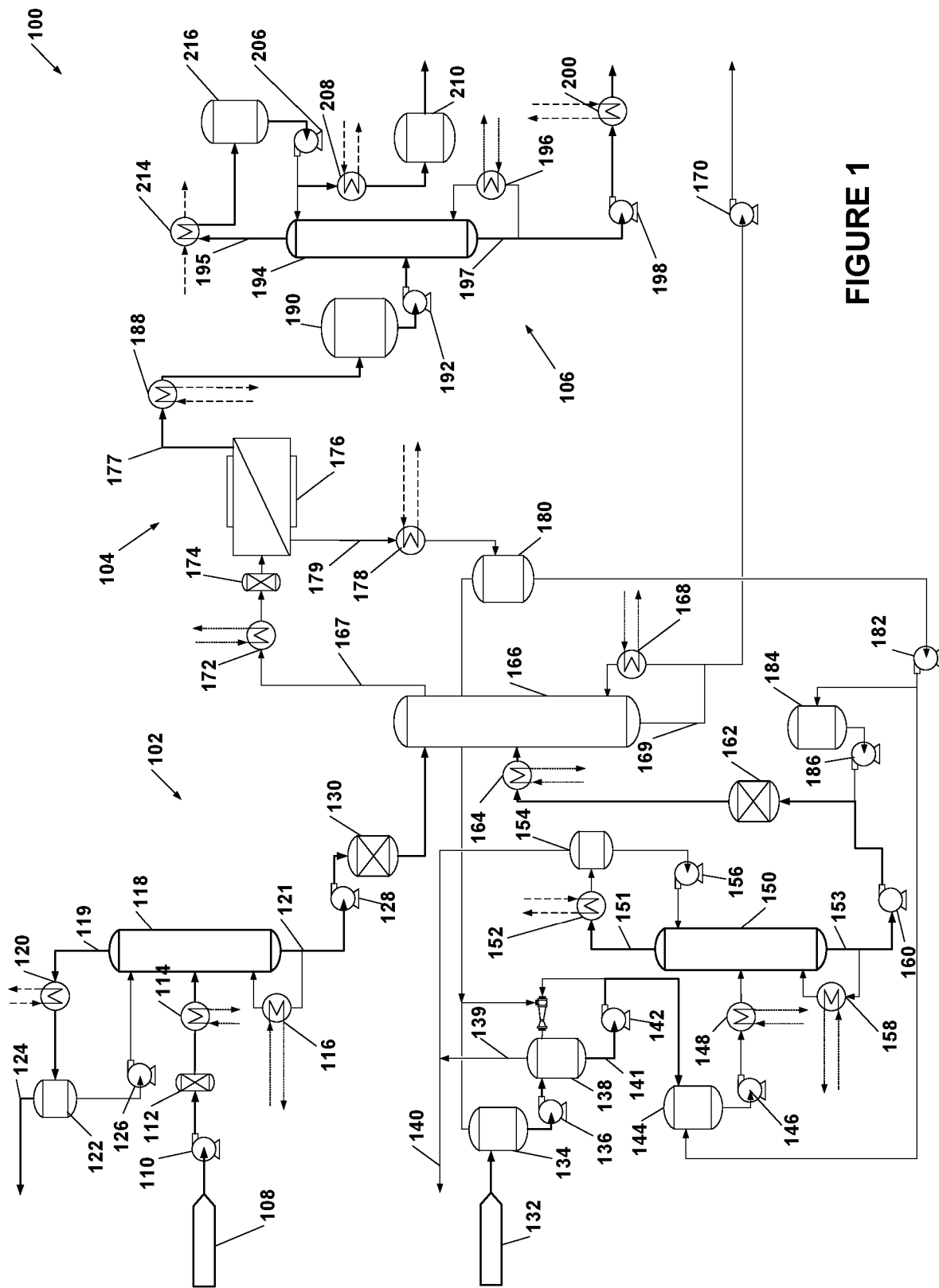
FIG. 1 illustrates an ethanol production system having two low boilers removal distillation columns, according to an aspect of the present disclosure.

The present disclosure provides high-grade ethanol production systems and methods that increase energy efficiency as compared to typical systems and methods by minimizing undesired acetal formation. In some aspects, the provided ethanol production method may include a low boilers removal process followed by a water removal process followed by a high boilers removal process. In some instances, a portion or all of the acetal in a feed stream may be removed as part of the low boilers removal process. Acidity (e.g., carbon dioxide) may be removed from a feed stream prior to or during the low boilers removal process. The order of processes in such aspects (low boiler removal followed by water removal followed by high boiler removal) helps minimize acetal production by removing the low boiling components acetaldehyde and ethyl acetate before the dehydration step. The continuous production of acetal during dehydration that is seen in typical systems is therefore minimized or eliminated since there is no acetaldehyde remaining in the dehydration system's feed stream that can convert to acetal. Acetal production can also be minimized by removing the acidity and/or a portion of acetal before the dehydration step. Removing the acidity from the system removes the catalyst for the acetal formation reaction.

By minimizing acetal production, the provided method minimizes the amount of energy that is required to remove acetal when producing high-grade ethanol. The provided method additionally minimizes acetal production without the use of chemicals. Further, the provided method makes it feasible to produce high-grade ethanol while minimizing or eliminating a loss of yield or conversion. For instance, the provided system may produce both high-grade ethanol and fuel-grade ethanol from received feed ethanol, which helps maximize the amount of system output that is used compared to the system input.

Regen and/or 190P or any other combination of ethanol streams may be fed to the provided system. For instance, the provided system may be an add-on to existing fuel-grade ethanol production systems or plants. In some aspects, the provided high-grade ethanol production system includes a low boilers removal subsystem connected to a subsequent water removal subsystem connected to a subsequent high boilers removal subsystem. It is known to a person having skill in the art that removing low boiling components in the presence of water is difficult. This is at least one reason why typical high-grade ethanol production processes remove water in a first step prior to the low boiler and high boilers removal steps. In at least some aspects, the presently disclosed production process may remove low boiling components in the presence of water while avoiding the negative consequences of excessive acetal production, thereby reducing energy consumption as compared to typical production processes. The low boilers removal subsystem may have various configurations to remove low boiling components from one or more feed streams.

In various examples, the low boilers removal subsystem may include a single distillation column. A 190P ethanol stream, regen ethanol stream, or other feed stream may each be directed to the low boilers removal distillation column. The low boilers removal distillation column generates an overhead stream that includes low boiling components, which is then removed (e.g., vented) from the system. In some instances, the overhead stream may include acetal as described below. The overhead stream may include carbon dioxide, which removes acidity from the feed stream. In some instances, at least a portion of the carbon dioxide contained in the feed stream may be removed prior to the feed stream reaching the low boilers removal distillation column. The low boilers removal distillation column also generates a bottom stream that is directed towards the water removal subsystem. In some instances, the 190P ethanol stream may alternatively be directed to a stripper column of the water removal system. The stripper column may be adapted to generate an overhead stream that removes (e.g., the overhead stream is vented) low boiling components from the 190P ethanol stream.

In other examples, the low boilers removal subsystem may include two distillation columns. A 190P ethanol stream or other feed stream may be directed to the first distillation column, which generates an overhead stream that removes (e.g., the overhead stream is vented) low boiling components from the 190P ethanol stream. The overhead stream may also remove acetal and/or carbon dioxide from the 190P ethanol stream. The first distillation column also generates a bottom stream that is directed towards the water removal subsystem. A regen ethanol stream or other feed stream may be directed to the second distillation column, which generates an overhead stream that removes (e.g., the overhead stream is vented) low boiling components from the regen ethanol stream. The overhead stream may also remove acetal and/or carbon dioxide from the regen ethanol stream. The second distillation column also generates a bottom stream that is directed towards the water removal subsystem. In some instances, at least a portion of the carbon dioxide contained in the regen ethanol stream may be removed prior to the regen ethanol stream reaching the low boilers removal distillation column.

In other examples, the low boilers removal subsystem may include a dual-use stripper column that is a component of both the low boilers removal subsystem and the water removal subsystem. A 190P ethanol stream may be directed to the stripper column. A regen ethanol stream may also be directed to the stripper column. In some instances, at least a portion of the carbon dioxide contained in the regen ethanol stream may be removed prior to the regen ethanol stream reaching the stripper column. The stripper column is adapted to generate an overhead stream that removes (e.g., the overhead stream is vented) low boiling components and any remaining carbon dioxide from the 190P and regen ethanol streams. In some instances, the stripper column, via the overhead stream, may remove a portion or all of the acetal in the feed streams directed to the stripper column.

The water removal subsystem includes a dehydration system that removes at least a portion of the water from an ethanol stream fed from the low boilers removal subsystem to the dehydration system. For instance, the dehydration system may be a system that employs reverse osmosis to separate water from a mixture of fluids. In some aspects, the water removal subsystem feeds an anhydrous ethanol stream to the high boilers removal subsystem. In some examples, the dehydration system may include a stripper column and a membrane (e.g., a semi-permeable membrane). The stripper column generates a vapor stream that is directed to contact the membrane. The membrane continuously removes water to produce anhydrous vapor. In some aspects, the membrane may be a polymer membrane. The polymer membrane may be built on hollow fibers. A selective layer may be placed on either the outside (e.g., shell side) or the inside (e.g., lumen side) of the hollow fibers. In other examples, the membrane may have other suitable forms that suitably dehydrate a feed vapor stream as part of a high-grade ethanol production process, such as tubular membranes including zeolites membranes or spiral wound membranes.

In other examples, the dehydration system may include a vaporizer and a molecular sieve unit (MSU). A vaporized stream from the vaporizer is directed to contact the MSU. The MSU may include two or three beds filled with zeolite pellets, which absorb water to produce anhydrous vapor until the zeolite pellets are saturated with water. A saturated zeolite pellet bed may be regenerated. For instance, freshly dehydrated ethanol may be directed to contact a saturated zeolite pellet bed to remove water from the saturated zeolite pellet bed, which produces a regenerate stream. The regenerate stream may have an ethanol concentration between 50-80 vol % and therefore must be recycled to upstream distillation for reprocessing. In instances in which the MSU includes multiple zeolite pellet beds, a saturated zeolite pellet bed may be regenerated while an unsaturated zeolite pellet bed is used to dehydrate a vaporized feed stream.

The high boilers removal subsystem includes a distillation column. The high boilers removal distillation column generates a bottom stream that includes high boiling components including acetals and fusels. The high boilers removal distillation column also generates an overhead stream of high-grade ethanol, which in some instances may be condensed and directed to storage. In at least some aspects, the high boilers removal distillation column's bottom stream meets the specifications for fuel-grade ethanol and may be directed to a 200P fuel loop. Some typical high-grade ethanol production systems may convert the entirety of an ethanol feed stream into high-grade ethanol. The provided system, conversely, may, in some instances, convert only a portion of an ethanol feed stream into high-grade ethanol, with a remaining portion converted into fuel-grade ethanol. The presently disclosed system's ability to produce both high-grade ethanol and fuel-grade ethanol provides flexibility of producing different grades of ethanol depending on the grade that is desired at any given time. At least some typical high-grade ethanol production systems do not offer this flexibility.

Various energy cascades between different components of the provided ethanol production systems may help increase their energy efficiency. For instance, the high boilers removal distillation column operates at a higher pressure than the low boilers removal distillation column to help with the separation of acetal. The difference in operating pressure enables energy cascading between the high boilers removal subsystem and the low boilers removal subsystem. Cascading may also be realized between (i) the high boilers removal subsystem and the water removal subsystem, (ii) the water removal subsystem (e.g., stripper column overhead stream or membrane retentate stream) and the low boilers removal subsystem, or (iii) distillation columns in the low boilers removal subsystem.

For example, a distillation column in the low boilers removal subsystem may be driven by (i) an overhead stream from the dual-use adapted stripper column, (ii) a second distillation column in the low boilers removal subsystem, (iii) retentate from the membrane of a water removal subsystem, or (iv) hot streams available in the ethanol plant that includes the provided system, such as a depressure stream or a 200P flash stream. In another example, overheads from the high boilers removal distillation column may be used as an energy source for the low boilers removal subsystem through a reboiler. In some aspects, the heat not used in the low boilers removal distillation column's reboiler may be utilized to heat cold streams (e.g., steam condensate, process water, scrubber water, 190P, regen, beer, etc.) within an ethanol plant that includes the provided system, or to heat cold streams (e.g., feed to stripper column, etc.) within the provided system.

In other examples, heat from the high boilers removal distillation column overheads may be utilized to directly heat cold streams (e.g., steam condensate, process water, scrubber water, 190P, regen, beer, etc.) within an ethanol plant that includes the provided system, or to heat cold streams (e.g., feed to stripper column, etc.) within the provided system. In another example, heat from the low boilers removal distillation column overheads may be utilized to directly heat cold streams (e.g., steam condensate, process water, scrubber water, 190P, regen, beer, etc.) within an ethanol plant that includes the provided system, or to heat cold streams (e.g., feed to stripper column, etc.) within the provided system. In another example, energy available from a membrane's retentate stream or an MSU's product stream (e.g., 200P) can be used to heat cold streams (e.g., steam condensate, process water, scrubber water, 190P, regen, beer, etc.) at the ethanol plant that includes the provided system.

Accordingly, the presently disclosed high-grade ethanol production systems and methods provide increased energy efficiency and greater flexibility in the final ethanol grade produced as compared to typical systems and methods. For example, typical systems and methods may consume twice as much energy as the present disclosed high-grade ethanol production systems and methods.

Various components of the presently disclosed systems may be in fluid communication with one another, such as through piping. Two components in fluid communication with one another may be in direct fluid communication (e.g., piping directly connects the two components) or may have intermediate components or processing between the two components, such as filters, pumps, heaters, odor removal vessels, etc.

Reference is made throughout this disclosure to high-grade ethanol. High-grade ethanol as used herein refers to the U.S. Pharmacopeia grade specifications for high-grade ethanol, which include at least 99.2 wt % ethanol, less than 200 ppm methanol, less than 10 ppm acetaldehyde and acetal combined, and less than 300 ppm of other organics (e.g., ethyl acetate and fusels). Reference is made throughout this disclosure to fuel-grade ethanol. Fuel-grade ethanol as used herein refers to ethanol product that includes a greater level of impurities (e.g., methanol, acetaldehyde, acetal, ethyl acetate, fusels) than high-grade ethanol.

FIG. 1 illustrates an example ethanol production system 100. The ethanol production system 100 includes a low boilers removal subsystem 102, a water removal system 104, and a high boilers removal subsystem 106. In various instances, an ethanol stream 108 (e.g., a 190P ethanol stream) and an ethanol stream 132 (e.g., a regen ethanol stream) may be fed to the low boilers removal subsystem 102. The ethanol stream 108 may be directed (e.g., via piping) towards a low boilers removal (LBR) distillation column 118 for the removal of low boiling components and all or a portion of acetal in the ethanol stream 108. In some aspects, the LBR distillation column 118 may remove carbon dioxide from the ethanol stream 108. A pump 110 may drive the ethanol stream 108 through piping towards the LBR distillation column 118. One or more filters 112 may be included along the piping. The ethanol stream 108 may be heated by a heater 114 prior to reaching the LBR distillation column 118. The LBR distillation column 118 generates an overhead stream 119 and a bottom stream 121. A reboiler 116 may drive the distillation separation that generates the overhead stream 119 and the bottom stream 121.

The overhead stream 119 includes low boiling components such as acetaldehyde and ethyl acetate. The overhead stream 119 may also include at least of portion of the acetal contained in the ethanol stream 108 and/or carbon dioxide. The low boiling components and any acetal and/or carbon dioxide from the overhead stream 119 are fully removed from the ethanol production system 100. For example, the overhead stream 119 may be directed to a venting system (e.g., a regenerative thermal oxidizer). In another example, the overhead stream 119 may be directed to storage for fuel-grade ethanol, to help recover the ethanol in the overhead stream 119 if it meets specifications for fuel-grade ethanol. The overhead stream 119 may be condensed via a condenser 120. The condensed overhead stream 119 may be directed to a condensation vessel 122. The condensation vessel 122 may generate a vent stream 124 that directs the low boiling components to the venting system. The condensation vessel 122 may generate a stream that is directed to the LBR distillation column 118, for example, via the pump 126.

In some aspects, the overhead stream 119 may include acetal so that the LBR distillation column 118 removes at least a portion of acetal from the ethanol stream 108. Acetal is a high boiling component. At atmospheric pressure, the boiling point of diethoxyethane (acetal) is 102° C. compared to acetaldehyde (20° C.), ethylacetate (77° C.), ethanol (78° C.), n-propanol (97° C.), water (100° C.), n-butanol (118° C.), and isoamyalcohol (132° C.). In the LBR distillation column 118, distillative removal of acetaldehyde and ethylacetate from ethanol and the higher molecular congeners is desired. Based on the above split of boiling point temperatures, a low boiler removal distillation column is typically operated to generate an overhead stream including acetaldehyde and ethylacetate and a bottom stream including ethanol and the remaining components (e.g., acetal). Such a split between the overhead stream and the bottom stream, however, does not always have to be the case.

In the presence of water, the sum of diethoxyethane (acetal), acetaldehyde, ethylacetate, ethanol, n-propanol, n-butanol, and isoamyalcohol forms complex polynary azeotropes based on numerous binary azeotropes and hetero azeotropes, including phase separation leasing to miscibility gaps. As a result of the complex polynary azeotropes formation, the LBR distillation column 118 may be configured to generate an overhead stream 119 that includes acetaldehyde, ethylacetate, and diethoxyethane (acetal), and a bottom stream 121 including ethanol, n-propanol, water, n-butanol, and isoamyalcohol. In some aspects, therefore, it may be beneficial to have low boilers removal subsystem 102 precede the water removal subsystem 104 so that low boilers removal occurs while water is present to take advantage of the complex polynary azeotropes formation.

The behavior of the complex polynary azeotropes formation, however, may change with the level of water concentration. As the water concentration of the feed stream to the LBR distillation column 118 decreases, acetal is increasingly removed with the bottom stream 121 given the boiling point splits among the components in the feed stream. In various instances, a level of water concentration in the feed stream to the LBR distillation column 118 may affect the amount of diethoxyethane (acetal) included in the overhead stream 119, with the remaining diethoxyethane (acetal) in the feed stream included in the bottom stream 121. As the water concentration in the feed stream decreases, the amount of diethoxyethane (acetal) included in the overhead stream 119 may decrease. The high boilers removal subsystem 106 may remove any remaining acetal in the ethanol production system 100. In some aspects, therefore, the water removal subsystem 104 may precede the low boilers removal subsystem 102 given the changing behavior with varying water level concentration.

The bottom stream 121 is directed towards the water removal system 104 in the example ethanol production system 100. The bottom stream 121 includes the ethanol stream 108 minus at least its low boiling components acetaldehyde and ethyl acetate. In some instances, the bottom stream 121 includes the ethanol stream 108 minus acetaldehyde, ethyl acetate, and carbon dioxide. In some instances, the bottom stream 121 includes the ethanol stream 108 minus acetaldehyde, ethyl acetate, carbon dioxide and at least a portion of the acetal in the ethanol stream 108. A portion of the bottom stream 121 may be supplied to the reboiler 116. The bottom stream 121 may be directed to one or more odor removal vessels 130 (e.g., via a pump 128) prior to reaching the water removal system 104. In various examples, the one or more odor removal vessels 130 include copper packing in two vessels to allow for cleaning/regeneration cycles. An advantage of such copper packing is that it eliminates the need to use carbon filters that need to be replaced frequently when saturated. Although it will be appreciated that carbon filters (e.g., activated carbon filters) or other suitable filters or suitable odor removal approaches may be employed.

The ethanol stream 132 may be directed towards an LBR distillation column 150 for the removal of low boiling components in the example ethanol production system 100. The ethanol stream 132 may be directed to a separation vessel 134 and then to a regen tank 138 (e.g., via a pump 136). The separation vessel 134 operates under vacuum and flashes at least a portion of the carbon dioxide from the ethanol stream 132 out as an overhead stream. The overhead stream of carbon dioxide is pulled to the suction side of the educator connected to the regen tank 138. The regen tank 138 removes the overhead stream of carbon dioxide from the ethanol production system 100 via the acidity removal stream 139. The acidity removal stream 139 may direct the carbon dioxide to a venting system (e.g., a regenerative thermal oxidizer). Conventional ethanol production systems typically do not include the separation vessel 134 that separates at least a portion of the carbon dioxide contained in the ethanol stream 132 from the ethanol stream 132. The acidity removal stream 139 may join with the vent stream 140. Any remaining portion of the acidity (e.g., carbon dioxide) in the ethanol stream 132 may be removed via the LBR distillation column 150.

The ethanol stream 132 may be directed to a feed tank 144 (e.g., via a pump 142). A pump 146 may drive feed from the feed tank 144 towards the LBR distillation column 150. The feed may be heated by a heater 148 prior to reaching the LBR distillation column 150. The LBR distillation column 150 generates an overhead stream 151 and a bottom stream 153. A reboiler 158 may drive the distillation separation that generates the overhead stream 151 and the bottom stream 153.

The overhead stream 151 includes low boiling components such as acetaldehyde and ethyl acetate. The overhead stream 151 may also include carbon dioxide. In some instances, the LBR distillation column 150 may be configured to generate an overhead stream 151 that includes at least a portion of the acetal contained in the ethanol stream 132, as described above in connection with the LBR distillation column 118. The low boiling components and any acetal and/or carbon dioxide from the overhead stream 151 are fully removed from the ethanol production system 100. For example, the overhead stream 151 may be directed to a venting system (e.g., a regenerative thermal oxidizer). The overhead stream 151 may be condensed via a condenser 152. The condensed overhead stream 151 may be directed to a condensation vessel 154. In some examples, the condensation vessel 154 may generate a vent stream 140 that directs the low boiling components and any carbon dioxide to the venting system. In other examples, the vent stream 140 may be directed to storage for fuel-grade ethanol. The condensation vessel 154 may generate a stream that may be directed to the LBR distillation column 150, for example, via the pump 156.

The bottom stream 153 is directed towards the water removal system 104 in the example ethanol production system 100. The bottom stream 153 includes the ethanol stream 132 minus at least its low boiling components acetaldehyde and ethyl acetate. In some instances, the bottom stream 153 includes the ethanol stream 132 minus its low boiling components, at least a portion of the acetal contained in the ethanol stream 132, and carbon dioxide. A portion of the bottom stream 153 may be supplied to the reboiler 158. The bottom stream 153 may be directed to one or more odor removal vessels 162 (e.g., via a pump 160)

prior to reaching the water removal system 104. In various examples, the one or more odor removal vessels 162 are configured the same as the one or more odor removal vessels 130. For example, the one or more odor removal vessels 162 may include copper packing in two vessels to allow for cleaning/regeneration cycles. The one or more odor removal vessels 162 may remove mercaptans from a stream (e.g., the bottom stream 153) fed to the one or more odor removal vessels 162. A heater 164 may heat the bottom stream 153 prior to the bottom stream 153 being fed to the water removal subsystem 104.

In at least some aspects, the LBR distillation column 150 is configured to simultaneously remove acetaldehyde and acetal from a feed stream via the overhead stream 151. This may be due to the thermodynamics of boiling a polynary azeotrope in the presence of water, as described in more detail below.

The water removal subsystem 104 includes a dehydration system that removes water from an ethanol stream fed to the dehydration system. In various instances, the dehydration system might operate on fluids in liquid or gas states, or mixed states of liquid and gas. For example, the dehydration system might operate on at least a portion of the bottom stream 121 and/or at least a portion of the bottom stream 153, which are both liquids. In some examples, the dehydration system includes a stripper column 166 and one or more membranes 176 (e.g., vapor permeation membranes). In some aspects, the one or more membranes 176 may be a polymer membrane(s). The one or more membranes 176 may be built on hollow fibers. A selective layer may be placed on either the outside (e.g., shell side) or the inside (e.g., lumen side) of the hollow fibers in such instances. In other examples, the one or more membranes 176 may have other suitable forms that suitably dehydrate a feed vapor stream as part of a high-grade ethanol production process, such as tubular membranes including zeolites, adsorbents, or spiral wound membranes.

The stripper column 166 generates a vapor stream 167 and a bottom stream 169 from a feed stream (e.g., the bottom stream 121 and the bottom stream 153). A reboiler 168 may drive the stripper column 166. The vapor stream 167 is fed to the one or more membranes 176. The one or more membranes 176 may operate in parallel. Water is removed from the vapor stream 167 through the one or more membranes 176 to produce a retentate stream 177 (e.g., anhydrous ethanol). The retentate stream 177 includes ethanol and high boiling components (e.g., acetal and fusels), with the low boiling components, acidity, and water having been removed. The one or more membranes 176 may also generate a permeate stream 179 when contacted with the vapor stream 167. In various instances, the vapor stream 167 may be directed through a heater 172 and/or one or more filters 174 prior to reaching the one or more membranes 176.

The permeate stream 179 may be condensed via a condenser 178 and directed to a permeate vessel 180. From the permeate vessel 180, a portion of the permeate stream 179 is directed to the regen tank 138. Another portion of the permeate stream 179 is directed to the feed tank 144 and/or the feed tank 184 (e.g., via a pump 182). The permeate stream 179 directed to the feed tank 184 may be further directed to the stripper column 166 (e.g., via the pump 186). The bottom stream 169 of the stripper column 166 may be directed to other areas of an ethanol plant including the example ethanol production system 100, for example, via the pump 170. A portion of the bottom stream 169 may be supplied to the reboiler 168.

The retentate stream 177 may be condensed via the condenser 188 and directed to a retentate vessel 190. Retentate from the retentate vessel 190 may be directed to the high boilers removal subsystem 106, for example, via the pump 192.

The high boilers removal subsystem 106 includes a high boilers removal (HBR) distillation column 194 in the example ethanol production system 100. The HBR distillation column 194 generates an overhead stream 195 and a bottom stream 197. A reboiler 196 may drive the distillation separation that generates the overhead stream 195 and the bottom stream 197. The bottom stream 197 includes high boiling components such as acetal and fusels. In some instances, the low boilers removal subsystem 102 may not remove, or may not fully remove, acetal from the ethanol streams 108 and 132. Moreover, the water removal subsystem 104 may generate acetal in at least some instances. The high boilers removal subsystem 106 therefore may remove remaining acetal in the bottom stream 197 so that the overhead stream 195 includes high-grade ethanol. In at least some aspects, the bottom stream 197 meets specifications for fuel-grade ethanol and therefore may be directed towards storage (e.g., via the pump 198). The bottom stream 197 may be cooled by a cooler 200 prior to reaching storage.

The overhead stream 195 includes high-grade ethanol and may be directed to a storage tank 210. Between the HBR distillation column 194 and the storage tank 210, the overhead stream 195 may, in some instances, be condensed via a condenser 214 and directed to a vessel 216. High-grade ethanol in the vessel 216 may be directed towards the storage tank 210 (e.g., via the pump 206). A portion of the high-grade ethanol in vessel 216 may be directed back to the HBR distillation column 194 as reflux. The high-grade ethanol may be cooled by a cooler 208 prior to reaching the storage tank 210.

Figure 2:
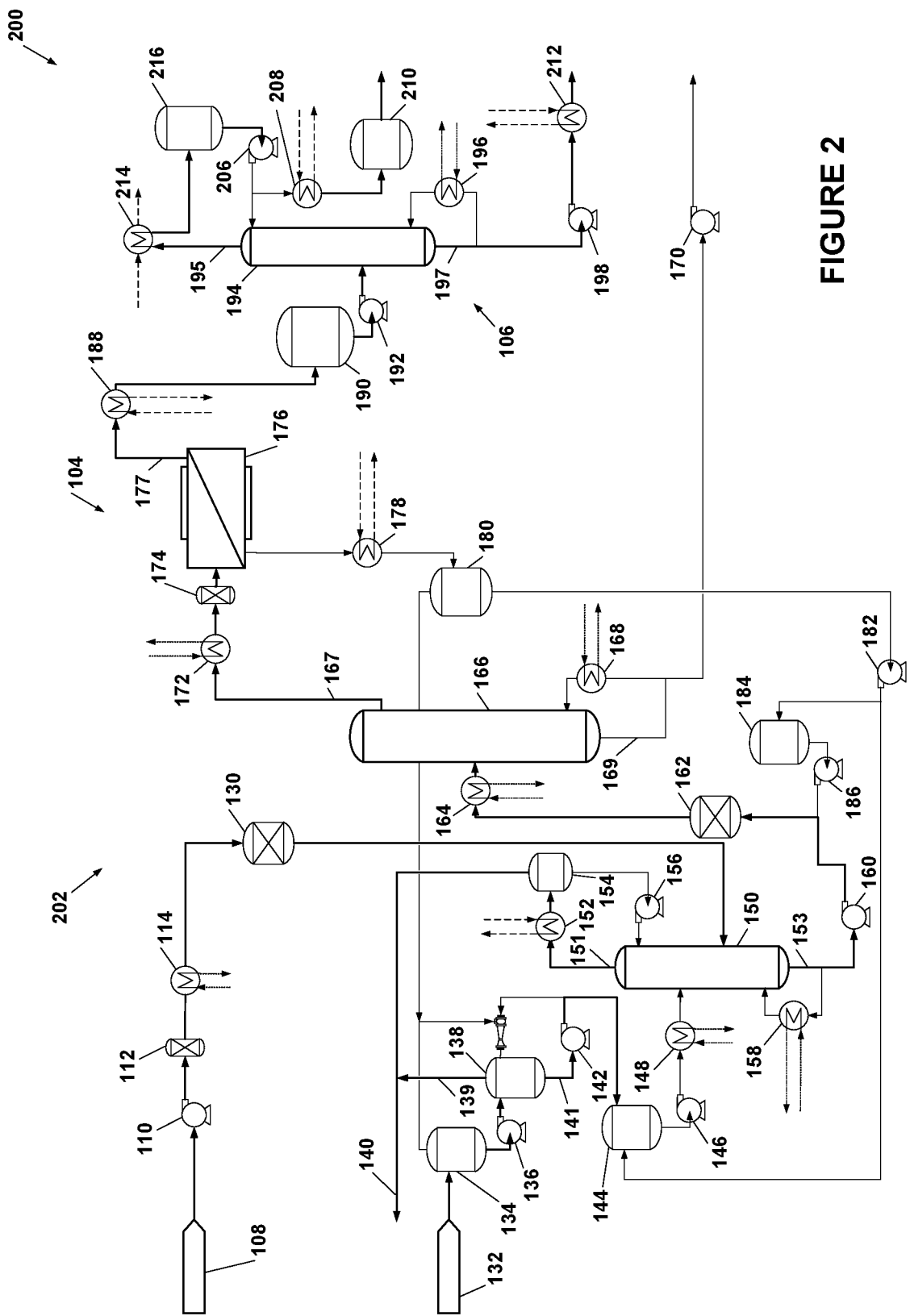
FIG. 2 illustrates an ethanol production system having one low boilers removal distillation column, according to an aspect of the present disclosure.

FIG. 2 illustrates an example ethanol production system 200. The ethanol production system 200 includes a low boilers removal subsystem 202, the water removal system 104, and the high boilers removal system 106. The low boilers removal subsystem 202 is similar to the low boilers removal subsystem 102 except that the ethanol stream 108 is directed to the LBR distillation column 150. Stated differently, in the low boilers removal subsystem 102, the low boiling components were removed from the ethanol stream 108 via the LBR distillation column 118 and the low boiling components were removed from the ethanol stream 132 via the LBR distillation column 150. In the low boilers removal subsystem 202, the low boiling components are instead removed (e.g., the vent stream 140) from both the ethanol stream 108 and the ethanol stream 132 via the LBR distillation column 150. The LBR distillation column 150 may also remove at least a portion of the acetal contained in the ethanol streams 108 and 132 and/or any remaining carbon dioxide from the ethanol stream 108 and the ethanol stream 132, as described above.

Figure 3:
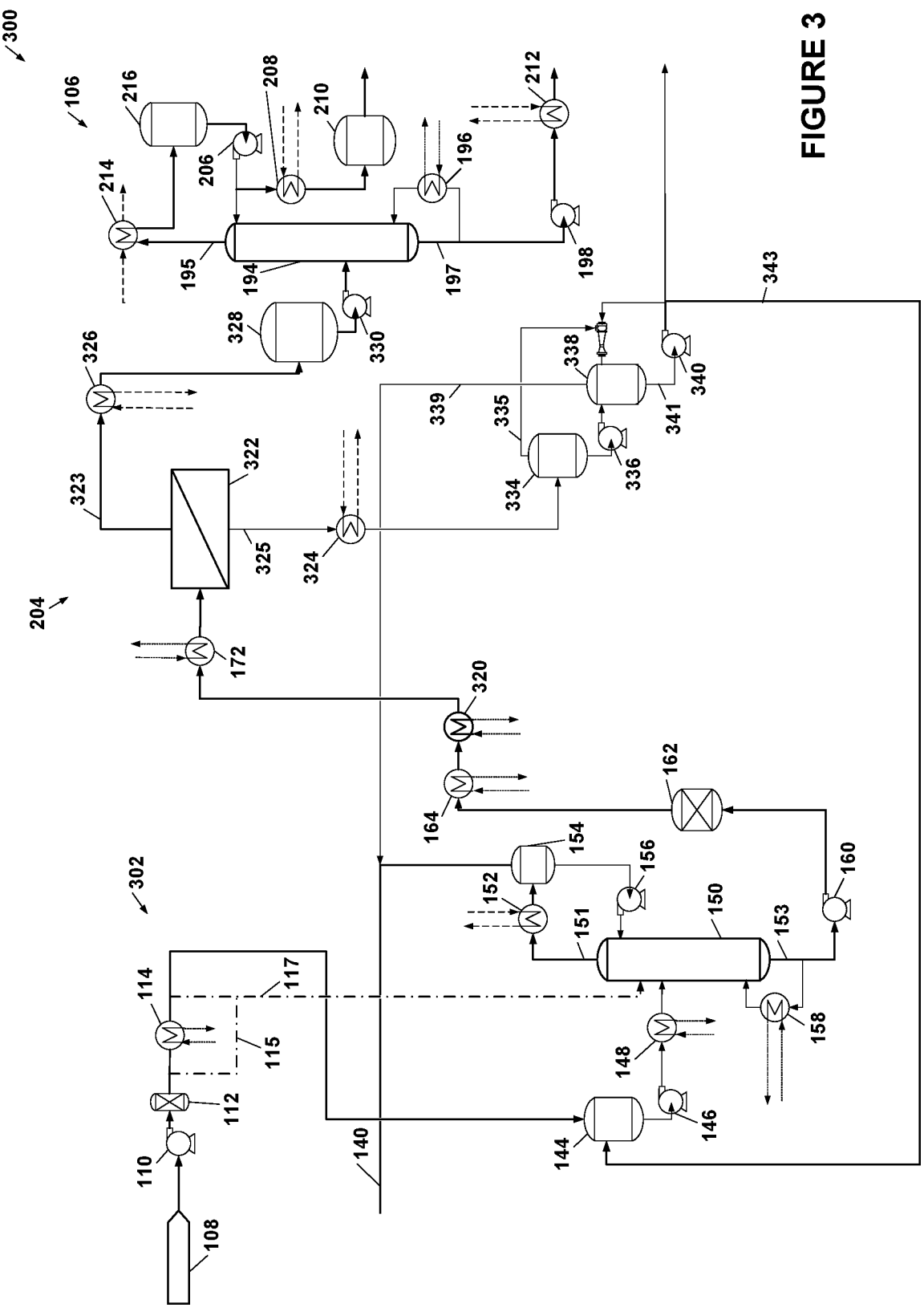
FIG. 3 illustrates an ethanol production system having a dehydration system including a vaporizer and a molecular sieve unit, according to an aspect of the present disclosure.

FIG. 3 illustrates an example ethanol production system 300. The ethanol production system 300 includes a low boilers removal subsystem 302, a water removal subsystem 204, and the high boilers removal subsystem 106. In various instances, the ethanol stream 108 (e.g., a 190P ethanol stream) may be fed to the low boilers removal subsystem 302. The ethanol stream 108 may be directed towards the LBR distillation column 150 for the removal of low boiling components. The LBR distillation column 150 may also remove at least a portion of the acetal contained in the ethanol stream 108 and/or carbon dioxide in the ethanol stream 108. In some examples, the ethanol stream 108 may be directed straight to the LBR distillation column 150 (e.g., via the stream 117). In other examples, the ethanol stream 108 may be directed to the feed tank 144 prior to reaching the LBR distillation column 150. A pump 110 may drive the ethanol stream 108 through piping towards the feed tank 144. One or more filters 112 may be included along the piping. In some examples, the ethanol stream 108 may be heated by the heater 114 prior to reaching the feed tank 144. In other examples, the ethanol stream 108 may bypass the heater 114 (e.g., via the stream 115).

Feed from the feed tank 144 is directed to the LBR distillation column 150 (e.g., via the pump 146). The feed may be heated by the heater 148 prior to being fed to the LBR distillation column 150. The LBR distillation column 150 generates the overhead stream 151 and the bottom stream 153. The reboiler 158 may drive the distillation separation that generates the overhead stream 151 and the bottom stream 153.

The overhead stream 151 includes low boiling components such as acetaldehyde and ethyl acetate. In some instances, the overhead stream 151 may include at least a portion of the acetal contained in the ethanol stream 108 and/or carbon dioxide, as described above. The low boiling components and any acetal and/or carbon dioxide from the overhead stream 151 are fully removed from the ethanol production system 300. For example, the overhead stream 151 may be directed to a venting system (e.g., a regenerative thermal oxidizer). The overhead stream 151 may be condensed via the condenser 152. The condensed overhead stream 151 may be directed to the condensation vessel 154. The condensation vessel 154 may generate a vent stream 140 that directs the low boiling components and any carbon dioxide to the venting system. In another example, the vent stream 140 may be directed to storage for fuel-grade ethanol. The condensation vessel 154 may generate a stream that is directed to the LBR distillation column 150, for example, via the pump 156.

The bottom stream 153 is directed towards the water removal system 204. The bottom stream 153 includes the ethanol stream 108 minus at least its low boiling components acetaldehyde and ethyl acetate. In some instances, the bottom stream 153 includes the ethanol stream 132 minus its low boiling components and carbon dioxide. In some instances, the bottom stream 153 includes the ethanol stream 132 minus its low boiling components, carbon dioxide, and at least a portion of the acetal contained in the ethanol stream 132. A portion of the bottom stream 153 may be supplied to the reboiler 158. The bottom stream 153 may be directed to one or more odor removal vessels 162 (e.g., via a pump 160) prior to reaching the water removal system 204. The heater 164 may heat the bottom stream 153 prior to the bottom stream 153 being fed to the water removal subsystem 204.

The water removal subsystem 204 includes a dehydration system that removes water from an ethanol stream fed to the dehydration system. In some examples, the dehydration system includes a vaporizer 320 and a molecular sieve unit (MSU) 322. The vaporizer 320 vaporizes an ethanol feed stream and the MSU 322 dehydrates the vaporized stream. In various instances, the heater 172 heats the vaporized stream prior to the vaporized stream contacting the MSU 322.

The MSU 322 generates an anhydrous ethanol stream 323 and a regenerate stream 325. The regenerate stream 325 is condensed via a condenser 324. The condensed regenerate stream 325 may be directed to a separation vessel 334 and then to a regen tank 338 (e.g., via a pump 336). The separation vessel 334 operates under vacuum and flashes at least a portion of the carbon dioxide from the regenerate stream 325 out as an overhead stream. The overhead stream of carbon dioxide is pulled (e.g., via the stream 335) to the suction side of the educator connected to the regen tank 338. The regen tank 338 removes the overhead stream of carbon dioxide from the ethanol production system 300 via the acidity removal stream 339. The acidity removal stream 339 may direct the carbon dioxide to a venting system (e.g., a regenerative thermal oxidizer). The acidity removal stream 339 may join with the vent stream 140. In various instances, a stream 341 from the regen tank 338 may be directed to a rectifier (e.g., via a pump 340). In various instance, a stream 343 from the regen tank 338 may be directed to the feed tank 144.

The anhydrous ethanol stream 323 generated by the MSU 322 is directed towards the high boilers removal subsystem 106. The anhydrous ethanol stream 323 may be condensed via a condenser 326 and directed to a vessel 328. Anhydrous ethanol from the vessel 328 may be directed to the high boilers removal subsystem 106, for example, via the pump 330. The high boilers removal subsystem 106 generates high-grade ethanol product and fuel-grade ethanol product, as described above, from the anhydrous ethanol fed to the high boilers removal subsystem 106.

Figure 4:
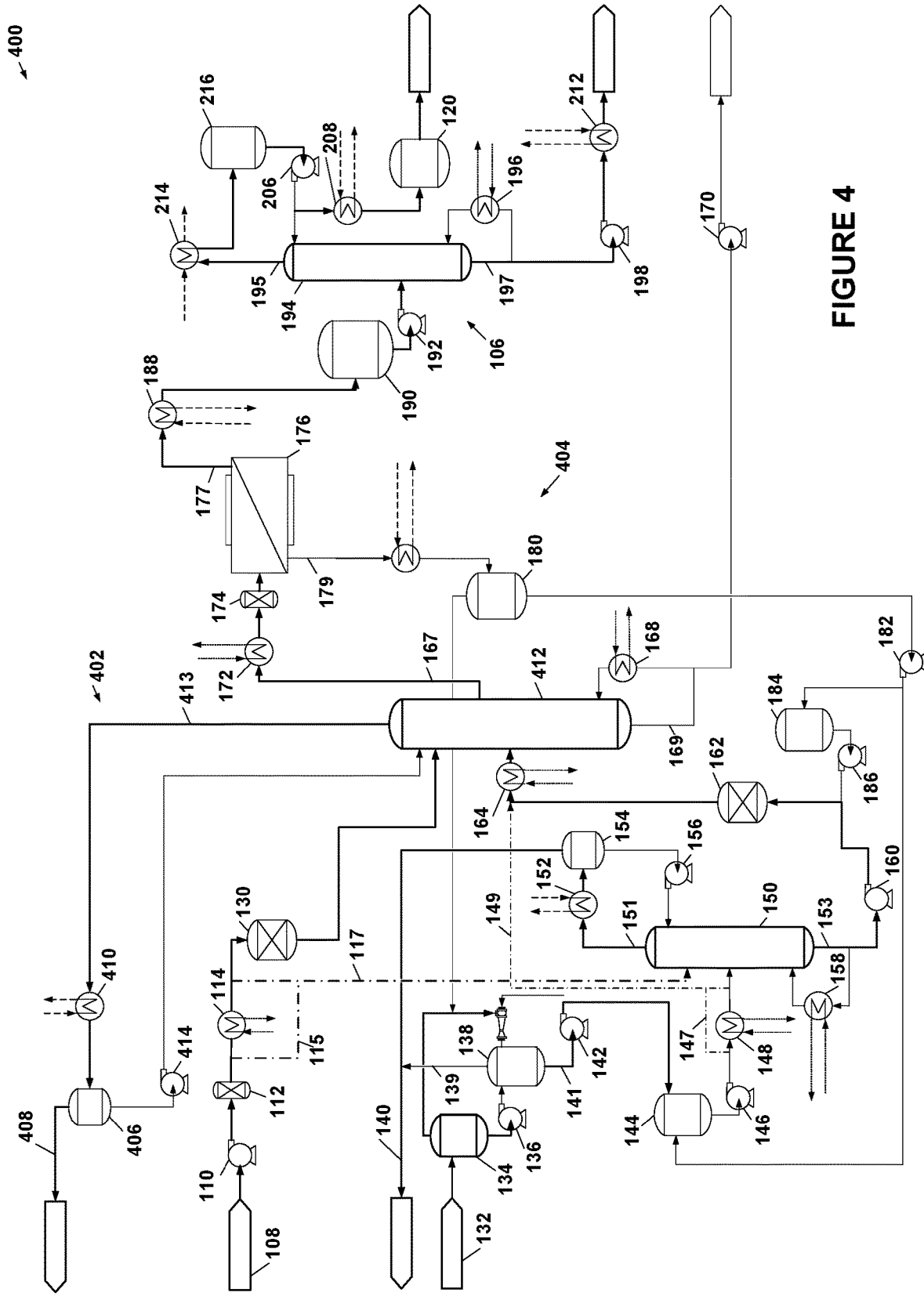
FIG. 4 illustrates an ethanol production system having a dehydration system including a stripper column configured to remove low boiling components, according to an aspect of the present disclosure.

FIG. 4 illustrates an example ethanol production system 400. The ethanol production system 400 includes a low boilers removal subsystem 402, a water removal subsystem 404, and the high boilers removal subsystem 106. In particular, the ethanol production system 400 includes a stripper column 412 that is adapted to both (i) provide a feed stream (e.g., the vapor stream 167) to the one or more membranes 176 and (ii) remove low boiling components from the ethanol production system 400. The stripper column 412 may also be adapted to remove at least a portion of acetal and/or carbon dioxide from a stream fed to the stripper column 412, as described above in connection with the LBR distillation column 150. For example, the stripper column 412 may include vent condensation equipment to aid in the removal of the low boiling components, acetal, and/or carbon dioxide. The stripper column 412 can therefore be considered a component of both the low boilers removal subsystem 402 and the water removal subsystem 404.

The stripper column 412 generates from a feed stream the vapor stream 167 and the bottom stream 169, as described above. The stripper column 412 also generates an overhead stream 413. The overhead stream 413 includes low boiling components such as acetaldehyde and ethyl acetate. The overhead stream 413 may also include at least a portion of the acetal contained the feed stream and/or carbon dioxide, as described above. The low boiling components and any acetal and/or carbon dioxide from the overhead stream 413 are fully removed from the ethanol production system 400. For example, the overhead stream 413 may be directed to a venting system (e.g., a regenerative thermal oxidizer) via vent condensation equipment. In another example, the overhead stream 413 may be directed to storage for fuel-grade ethanol, to help recover the ethanol in the overhead stream 413 if it meets specifications for fuel-grade ethanol. The overhead stream 413 may be condensed via a condenser 410. The condensed overhead stream 413 may be directed to a condensation vessel 406. The condensation vessel 406 may generate a vent stream 408 that directs the low boiling components to the venting system. The condensation vessel 406 may generate a stream that is directed to the stripper column 412, for example, via a pump 414.

In various instances, the ethanol stream 108 (e.g., a 190P ethanol stream) and the ethanol stream 132 (e.g., a regen ethanol stream) may be fed to the low boilers removal subsystem 402. In some instances, the entirety of the ethanol stream 108 may be directed towards the stripper column 412 for the removal of low boiling components in the ethanol stream 108. In some instances, the stripper column 412 may remove at least a portion of the acetal contained in the ethanol stream 108 and/or carbon dioxide from the ethanol stream 108, as described above. The pump 110 may drive the ethanol stream 108 towards the stripper column 412. One or more filters 112 may be included along the piping. In some examples, the ethanol stream 108 may be heated by the heater 114 prior to reaching the stripper column 412. In other examples, the ethanol stream 108 may bypass the heater 114 (e.g., via the stream 115). In various aspects, the ethanol stream 108 may be directed to one or more odor removal vessels 130 prior to reaching the stripper column 412. The stripper column 412 generates the overhead stream 413 that removes the low boiling components and any carbon dioxide from the ethanol stream 108.

In some instances, only a portion of the ethanol stream 108 is directed towards the stripper column 412. In such instances, a portion of the ethanol stream 108 may be directed towards the LBR distillation column 150, for example, via the stream 117. The LBR distillation column 150 removes low boiling components from this portion of the ethanol stream 108. In some instances, the LBR distillation column 150 may remove at least a portion of the acetal contained in the ethanol stream 108 and/or carbon dioxide from the ethanol stream 108, as described above. In at least one example, the entirety of the ethanol stream 108 may be directed towards the LBR distillation column 150.

In various aspects, low boiling components, and in some instances acetal and/or carbon dioxide, may be removed from the ethanol stream 132 in the same manner as the low boilers removal subsystem 102, in which the entirety of the ethanol stream 132 may be directed towards the LBR distillation column 150. In other aspects, at least a portion of the ethanol stream 132 may be directed towards the stripper column 412 for the removal of low boiling components, for example, via the stream 149. In some instances, at least a portion of the acetal contained in the ethanol stream 132 and/or carbon dioxide may be removed by the stripper column 412, for example, via the stream 149. Accordingly, in the ethanol production system 400, any combination of the ethanol stream 108 and the ethanol stream 132 may be directed towards the stripper column 412 and/or the LBR distillation column 150 for the removal of low boiling components, and in some instances acetal and/or any carbon dioxide. The stream 147 illustrates that the feed from the feed tank 144 may bypass the heater 148 in some instances.

In at least some aspects, the stripper column 412 is configured to simultaneously remove acetaldehyde and acetal from a feed stream via the overhead stream 413. Simultaneously removing acetaldehyde and acetal via the stripper column 412 enables different sequences of the low boilers removal subsystem, the water removal subsystem, and the high boilers removal subsystem in the provided ethanol production system. For instance, the water removal subsystem 404 including the stripper column 412 may be positioned prior to, or upstream, the low boilers removal subsystem 102 in one example. The different sequence orders of the provided ethanol production system and method are discussed more in connection with FIGS. 6B and 6C.

The water removal subsystem 404 is similar to the water removal subsystem 104 except that the water removal subsystem 404 includes the stripper column 412 that is adapted as described above. After water is removed via the water removal subsystem 404, high boiling components may be removed via the high boilers removal subsystem 106 as described above.

Figure 5:
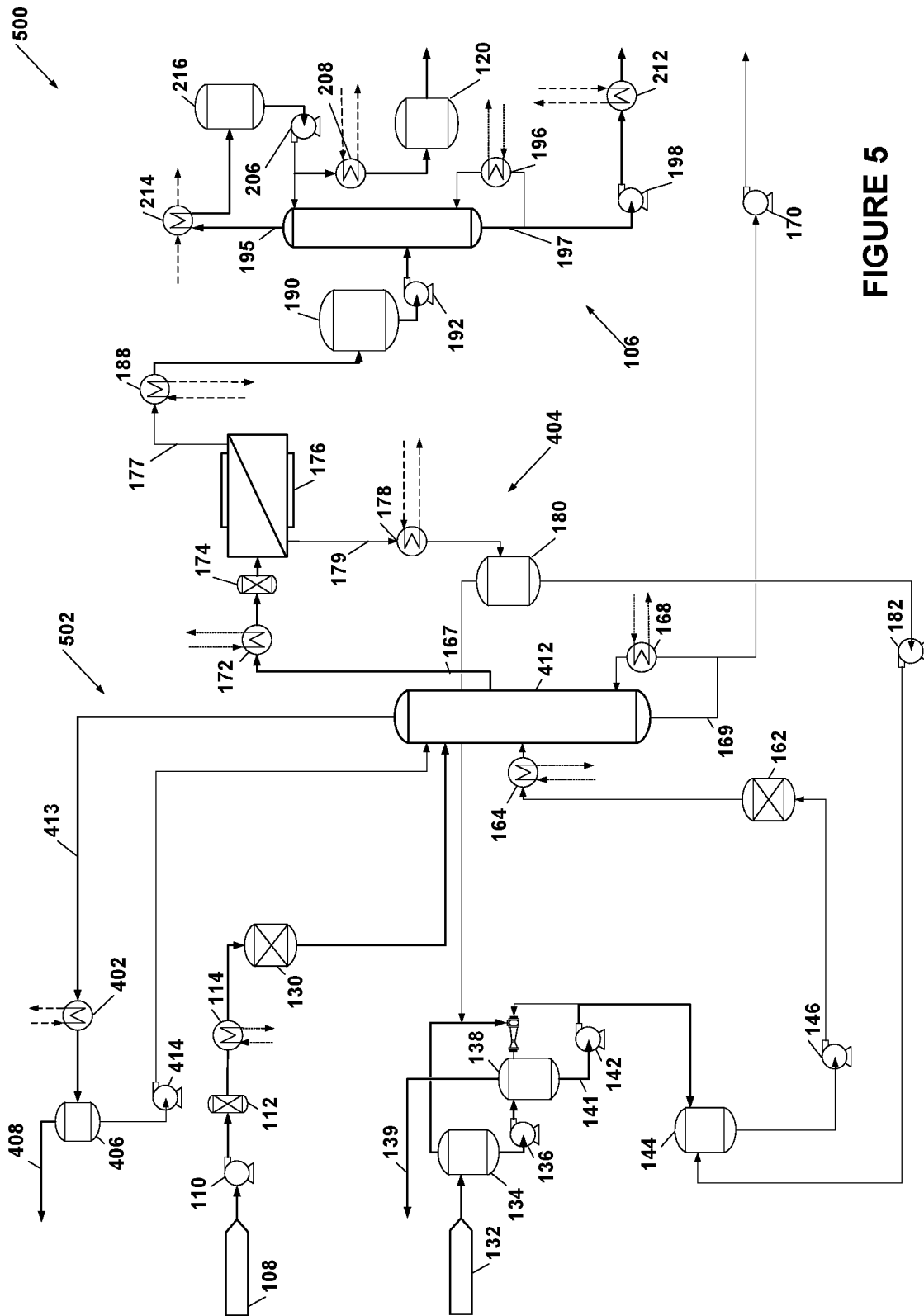
FIG. 5 illustrates an ethanol production system configured to remove low boiling components without the use of a low boilers removal distillation column, according to an aspect of the present disclosure.

FIG. 5 illustrates an example ethanol production system 500 in which the entirety of the ethanol stream 108 and the entirety of the ethanol stream 132 are directed towards the stripper column 412. The stripper column 412 may remove low boiling components, and in some instances at least a portion of the acetal contained in the ethanol streams 108 and 132 and/or carbon dioxide, from the ethanol streams 108 and 132, as described above. The ethanol production system 500 includes a low boilers removal subsystem 502, the water removal subsystem 404, and the high boilers removal subsystem 106. Directing the entirety of the ethanol streams 108 and 132 to the stripper column 412 eliminates the need for the LBR distillation column 150 and its corresponding components (e.g., vent condensation components) in the low boilers removal subsystem 502 as compared to the low boilers removal subsystem 402.

The stripper column 412 generates the overhead stream 413 that includes low boiling components from the ethanol streams 108 and 132, and removes (e.g., directs to a venting system) the low boiling components from the ethanol production system 500. In some instances, the overhead stream 413 may include at least a portion of the acetal contained in the ethanol streams 108 and 132 and/or carbon dioxide to remove such components from the ethanol production system 500. The stripper column 412 also generates the vapor stream 167 that is fed to the one or more membranes 176 to dehydrate the vapor stream 167. After dehydration, the high boilers removal subsystem 106 removes the high boiling components as described above.

It will be appreciated that various combinations of the low boilers removal subsystems 102, 202, 302, 402, and 502, the water removal subsystems 104, 204, and 404, and the high boilers removal subsystem 106 may be realized. For example, a water removal subsystem 204 including a dehydration system having a vaporizer 320 and a MSU 322 may be included in combinations other than with a low boilers removal subsystem 302 and a high boilers removal subsystem 106.

While the preceding paragraphs describe the provided ethanol production methods and systems as including a low boilers removal process followed by a water removal process followed by a high boilers removal process, in various aspects, the provided system may include components that enable a rearrangement of these processes. In such aspects, the provided system may include a low boilers removal distillation column (e.g., the LBR distillation columns 118 and 150) and/or a stripper column (e.g., the stripper column 412) constructed to simultaneously remove at least a portion of the acetaldehyde and at least a portion of the acetal from a feed stream, which enables rearranging the above-described low boilers removal, water removal, and high boilers removal subsystems while still overcoming the energy efficiency problems experienced by typical ethanol production systems having a water removal process prior to the removal of low and high boiling components.

For instance, the inventors have found that the thermodynamics of boiling a polynary azeotrope in the presence of water surprisingly enables removing significant amounts of acetal (boiling point of 102° C.) together with acetaldehyde (boiling point of 20° C.) via an overhead stream of a distillation or stripper column (e.g., the LBR distillation column 118 or 150 or the stripper column 412). In this way, large quantities of high boiling acetal may be removed in the presence of water at the top of the first column in the provided ethanol production system, which may be the LBR distillation column 150 or the stripper column 412 depending on the arrangement of the low boilers removal, water removal, and high boilers removal subsystems. Removing acetaldehyde and large quantities of acetal from the feed stream via the first column thereby helps minimize the amount of energy that is required to remove acetal when producing high-grade ethanol, as described above for ethanol production systems 100, 200, 300, 400, and 500. It should be noted that the provided ethanol production methods and systems including a low boilers removal process followed by a water removal process followed by a high boilers removal process (e.g., the ethanol production systems 100, 200, 300, 400, and 500) may also include a distillation or stripper column (e.g., the LBR distillation column 118 or 150 or the stripper column 412) constructed to simultaneously remove acetal and acetaldehyde and thus are not separate and distinct from the embodiments in which the processes are rearranged.

Figure 6A:
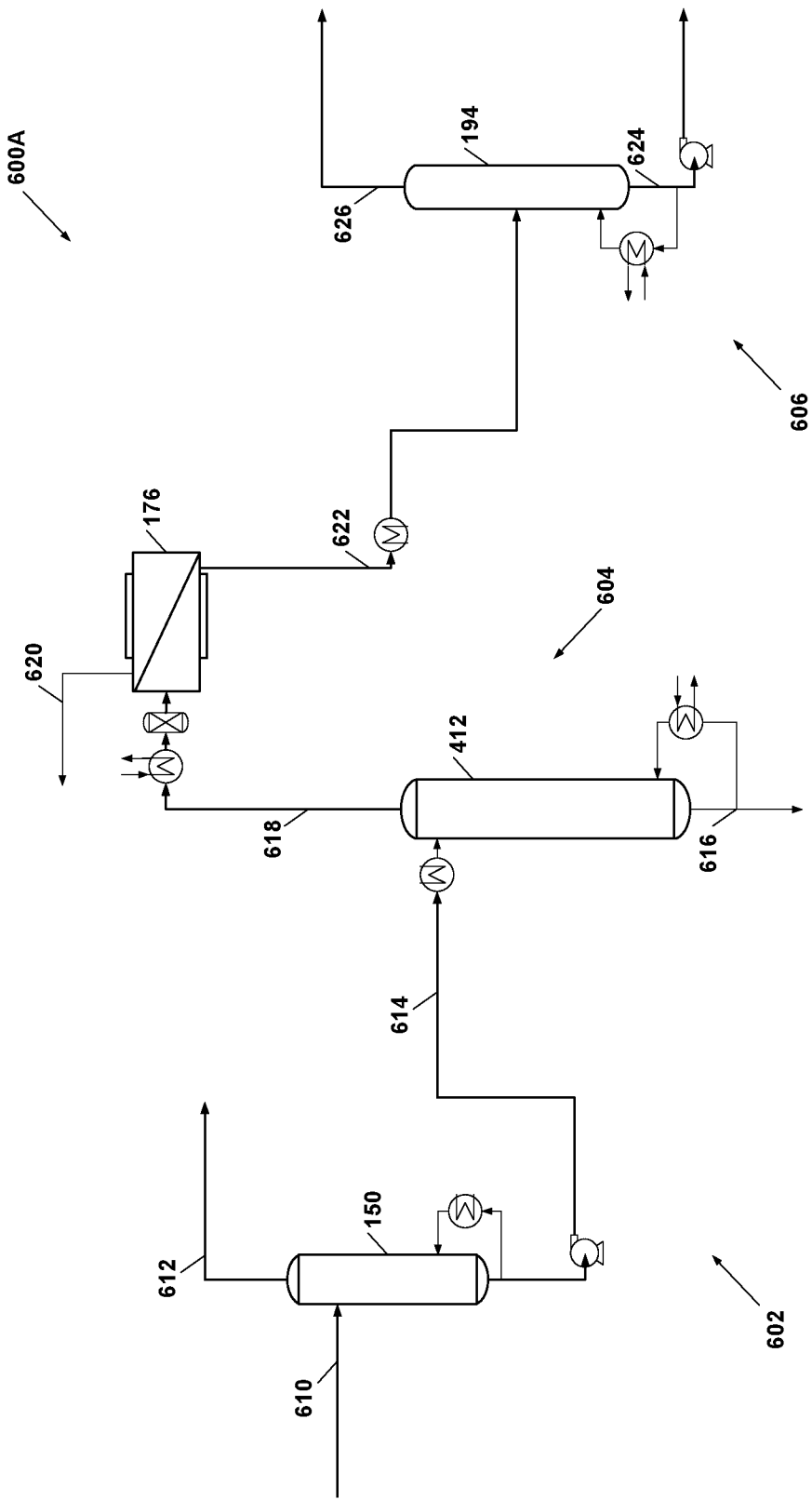
FIGS. 6A to 6C illustrate ethanol production systems having various configurations of a low boilers removal subsystem, a water removal subsystem, and a high boilers removal subsystem.
Figure 6B:
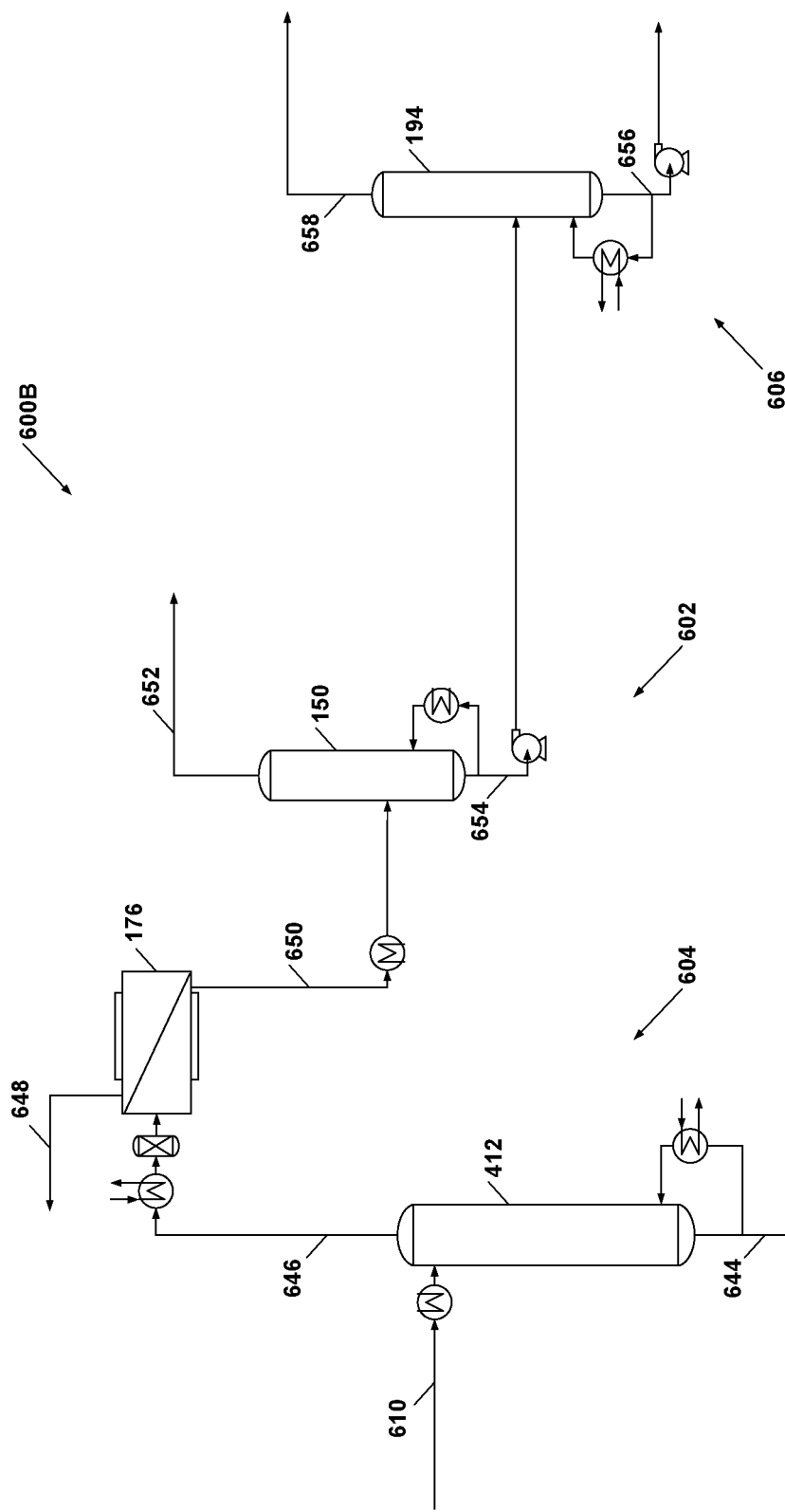
Figure 6C:
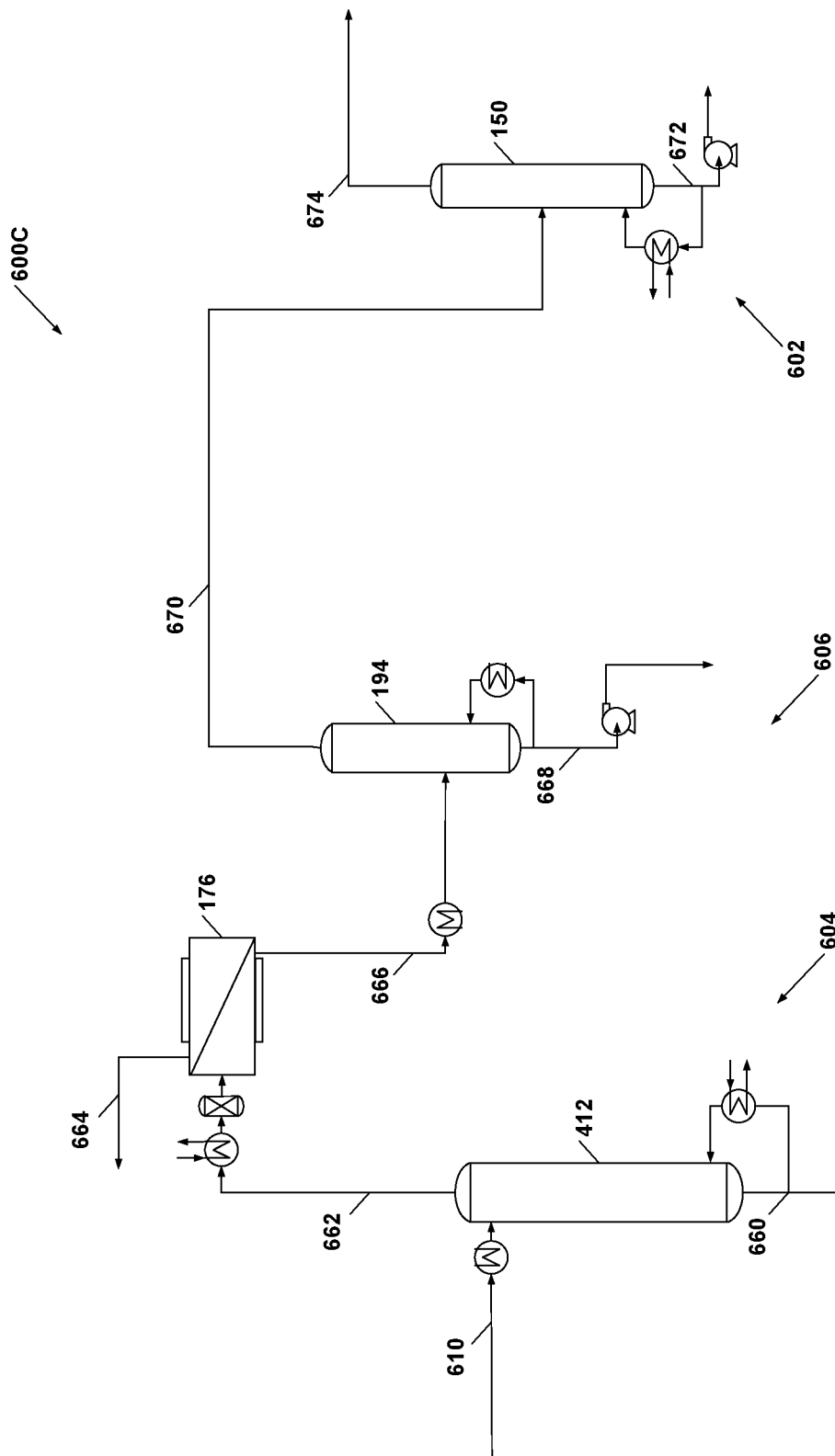

FIGS. 6A to 6C illustrate ethanol production systems 600A to 600C having various configurations of a low boilers removal subsystem 602, a water removal subsystem 604, and a high boilers removal subsystem 606. It should be appreciated that various intermediate components as described above in connection with the ethanol production systems 100, 200, 300, 400, and 500 have been omitted from the ethanol production systems 600A to 600C for the sake of simplicity.

FIG. 6A illustrates an example ethanol production system 600A in which the low boilers removal subsystem 602 precedes the water removal subsystem 604 which precedes the high boilers removal subsystem 606. For instance, the ethanol production system 600A may be configured according to the ethanol production systems 100, 200, 300, 400, or 500. The low boilers removal subsystem 602 may include the LBR distillation column 150. A stream 610 may be fed to the LBR distillation column 150 that includes carbon dioxide, acetaldehyde, ethylacetate, ethanol, water, acetal, mercaptans, and fusels. The LBR distillation column 150 may generate an overhead stream 612 that includes carbon dioxide, acetaldehyde, and ethylacetate. The overhead stream 612 may also include acetal. The LBR distillation column 150 may also generate a bottom stream 614 that includes ethanol, water, acetal, metacaptans, and fusels. The bottom stream 614 is fed to the water removal subsystem 604.

The water removal subsystem 604 may include the stripper column 412 and one or more membranes 176. The stripper column 412 may generate a bottom stream 616 that includes water. The stripper column 412 may also generate a vaporous stream 618 that is contacted with the one or more membranes 176 to produce a stream 620 and a stream 622. The stream 620 may include water. The stream 622 may include ethanol, acetal, and fusels and is directed to the high boilers removal subsystem 606. The high boilers removal subsystem 606 may include the HBR distillation column 194. The HBR distillation column 194 generates a bottom stream 624 that includes acetal and fusels. The HBR distillation column 194 also generates an overhead stream 626 that includes high-grade ethanol.

FIG. 6B illustrates an example ethanol production system 600B in which the water removal subsystem 604 precedes the low boilers removal subsystem 602 which precedes the high boilers removal subsystem 606. The stream 610 is fed to the stripper column 412 of the water removal subsystem 604. The stripper column 412 generates a bottom stream 644 that includes water. The stripper column 412 also generates a vaporous stream 646 that is directed to contact the one or more membranes 176 to produce a stream 648 and a stream 650. The stream 648 includes carbon dioxide, acetaldehyde, ethylacetate, ethanol, and water. The stream 650 includes carbon dioxide, acetaldehyde, ethylacetate, ethanol, acetal, mercaptans, and fusels and is directed to the low boilers removal subsystem 602. The LBR distillation column 150 generates an overhead stream 652 that includes carbon dioxide, acetaldehyde, ethylacetate, and ethanol. The LBR distillation column 150 also generates a bottom stream 654 that includes ethanol, acetal, mercaptans, and fusels.

The bottom stream 654 is directed to the high boilers removal subsystem 606. The HBR distillation column 194 generates a bottom stream 656 that includes acetal and fusels. The HBR distillation column 194 also generates an overhead stream 658 that includes high-grade ethanol.

FIG. 6C illustrates an example ethanol production system 600C in which the water removal subsystem 604 precedes the high boilers removal subsystem 606 which precedes the low boilers removal subsystem 602. The stream 610 is fed to the stripper column 412 of the water removal subsystem 604. The stripper column 412 generates a bottom stream 660 that includes water. The stripper column 412 also generates a vaporous stream 662 that is directed to contact the one or more membranes 176 to produce a stream 664 and a stream 666. The stream 664 includes carbon dioxide, acetaldehyde, ethylacetate, ethanol, and water. The stream 666 includes carbon dioxide, acetaldehyde, ethylacetate, ethanol, acetal, mercaptans, and fusels and is directed to the high boilers removal subsystem 606.

The HBR distillation column 194 of the high boilers removal subsystem 606 generates a bottom stream 668 that includes acetal and fusels. The HBR distillation column 194 also generates an overhead stream 670 that includes carbon dioxide, acetaldehyde, ethylacetate, and ethanol. The overhead stream 670 is directed to the low boilers removal subsystem 602. The LBR distillation column 150 of the low boilers removal subsystem 602 generates an overhead stream 674 that includes carbon dioxide, acetaldehyde, and ethylacetate. The LBR distillation column 150 also generates a bottom stream 672 that includes high-grade ethanol.

Figure 7A:
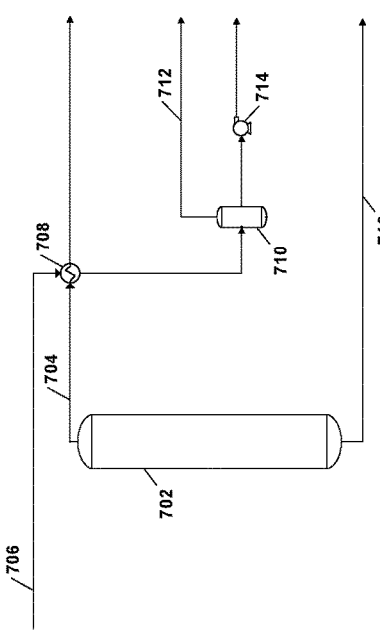
FIG. 7A illustrates a subsystem in which an overhead stream from a low boilers removal (LBR) distillation column exchanges heat with steam condensate, according to an aspect of the present disclosure.

As mentioned above, various energy cascades between different components of the provided ethanol production systems may help increase their energy efficiency. FIG. 7A illustrates a first example subsystem 700 in which an overhead stream 704 from a low boilers removal (LBR) distillation column 702 exchanges heat with steam condensate 706 to heat the steam condensate 706. In this example subsystem 700, steam condensate liquid may flow through a line and exchange heat with an LBR distillation column overhead stream at a condenser 708. After being heated, steam condensate vapor and liquid may flow to a steam flash vessel 710. The steam flash vessel 710 may produce a flash steam 712 that may be used in other areas of an ethanol production plant. In at least some aspects, steam condensate may be pumped by a pump 712 from the steam flash vessel 710 to other areas of the ethanol production plant. A bottom stream 716 generated by the LBR distillation column 702 may be directed as described for any of the LBR distillation column bottom streams above.

Figure 7B:
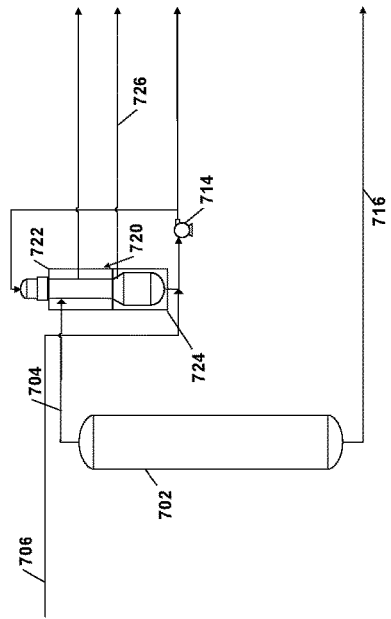
FIG. 7B illustrates a subsystem in which an overhead stream from a low boilers removal (LBR) distillation column exchanges heat with steam condensate, according to an aspect of the present disclosure.

FIG. 7B illustrates a second example subsystem 730 in which the overhead stream 704 from the low boilers removal (LBR) distillation column 702 exchanges heat with steam condensate 706 to heat the steam condensate 706. This example subsystem 730 includes a condenser 720. In at least some aspects, the condenser 720 includes a heat exchanger portion 722 and an evaporator body or flash vessel portion 724. The condenser 720 may function as an evaporator in this example. In at least some aspects, the heat exchanger portion 722 includes a shell and a tube. In this example subsystem 730, at least a portion of the liquid steam condensate 706 may flow into the tube side portion of the heat exchanger portion 722 of the condenser 720. In some aspects, there may be a pump (not illustrated) on the line through which the liquid steam condensate 706 flows. Such aspects may help increase the heat exchange area for better heat transfer. The LBR distillation column overhead stream 704 may be condensed in the shell side of the heat exchanger portion 722 of the condenser 720, which provides heat to the steam condensate 706 flowing through the tubes in the tube side portion. As such, steam condensate 706 will increase in temperature and can be partially vaporized. The steam condensate 706 of increased temperature may flow down to the evaporator body or flash vessel portion 724 of the condenser 720, which operates at a lower pressure than the heat exchanger portion 722. In the evaporator body or flash vessel portion 724, the steam condensate 706 will flash and generate low pressure steam 726 that can be used elsewhere in the ethanol production plant.

FIG. 8A illustrates a first example subsystem 800 in which an overhead stream 804 from a high boilers removal (HBR) distillation column 802 exchanges heat with steam condensate 706 to heat the steam condensate 706. The subsystem 800 is similar to the subsystem 700 except that an HBR distillation column overhead stream 804 heats the steam condensate 706 rather than the LBR distillation column overhead stream 704.

FIG. 8B illustrates a second example subsystem 830 in which the overhead stream 704 from the high boilers removal (HBR) distillation column 702 exchanges heat with steam condensate 706 to heat the steam condensate 706. The subsystem 830 is similar to the subsystem 730 except that an HBR distillation column overhead stream 804 flows to the condenser 720 rather than the LBR distillation column overhead stream 704 flowing to the condenser 720. The HBR distillation column overhead stream 804 may be condensed in the shell side of the heat exchanger portion 722 of the condenser 720, which provides heat to the steam condensate 706 flowing through the tubes in the tube side portion. As such, steam condensate 706 will increase in temperature and can be partially vaporized. The steam condensate 706 of increased temperature may flow down to the evaporator body or flash vessel portion 724 of the condenser 720. In the evaporator body or flash vessel portion 724, the steam condensate 706 will flash and generate low pressure steam 808 that can be used elsewhere in the ethanol production plant.

Figure 9A:
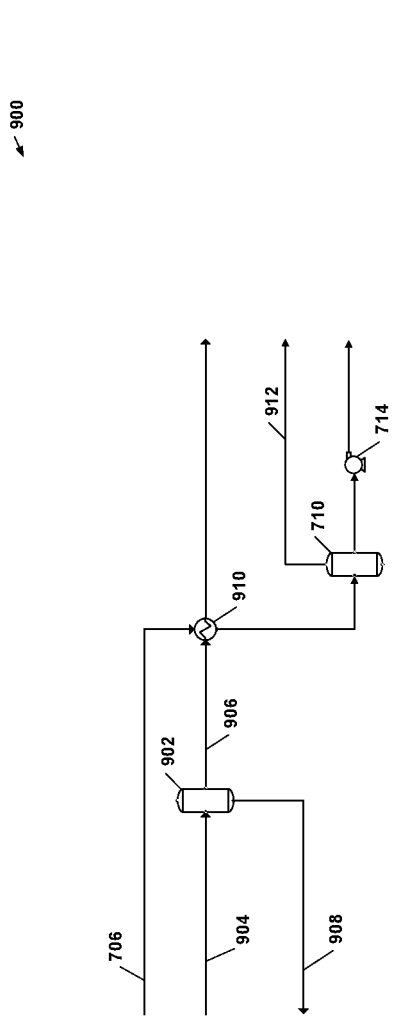
FIG. 9A illustrates a subsystem in which a retentate stream exchanges heat with steam condensate, according to an aspect of the present disclosure.

FIG. 9A illustrates a first example subsystem 900 in which a retentate stream 906 exchanges heat with steam condensate 706 to heat the steam condensate 706. The subsystem 900 may include a membrane 902 that is contacted by a feed stream 904 to thereby form the retentate stream 906 and a permeate stream 908. In this example subsystem 900, liquid steam condensate 706 may flow through a line and exchange heat with the retentate stream 906 from the membrane 902 at a condenser 910. After being heated, steam condensate 706 vapor and liquid may flow to a steam flash vessel 710. The steam flash vessel 710 may produce a flash steam 912 that may be used in other areas of an ethanol production plant. In at least some aspects, steam condensate 706 may be pumped by a pump 714 to other areas of the ethanol production plant. In some aspects, the subsystem 900 may include an MSU's product stream (e.g., 200P), instead of the retentate stream 906, that exchanges heat with the steam condensate 706 at the condenser 910.

Figure 9B:
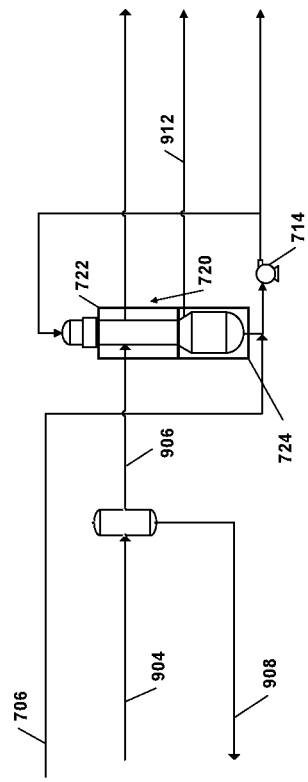
FIG. 9B illustrates a subsystem in which a retentate stream exchanges heat with steam condensate, according to an aspect of the present disclosure.

FIG. 9B illustrates a second example subsystem 930 in which a retentate stream 906 exchanges heat with steam condensate 706 to heat the steam condensate 706. This example subsystem 930 includes a condenser 720. The subsystem 930 is similar to the subsystems 730 and 830 except that a retentate stream 906 flows to the condenser 720 rather than the LBR distillation column overhead stream 704 or the HBR distillation column overhead stream 804 flowing to the condenser 720. The retentate stream 906 may be condensed in the shell side of the heat exchanger portion 722 of the condenser 720, which provides heat to the steam condensate 706 flowing through the tubes in the tube side portion. As such, steam condensate 706 will increase in temperature and can be partially vaporized. The steam condensate 706 of increased temperature may flow down to the evaporator body or flash vessel portion 724 of the condenser 720. In the evaporator body or flash vessel portion 724, the steam condensate 706 will flash and generate low pressure steam 912 that can be used elsewhere in the ethanol production plant. In some aspects, the subsystem 930 may include an MSU's product stream (e.g., 200P), instead of the retentate stream 906, that exchanges heat with the steam condensate 706 at the condenser 720.

In various aspects, the provided systems (e.g., the ethanol production systems 100, 200, 300, 400, or 500) may include one or more of the subsystems 700, 710, 800, 810, 900, and 910.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. An ethanol production method comprising:
   a low boilers removal process including:
      receiving at a first distillation column, a first feed stream including ethanol, low boiling components having associated boiling points lower than a boiling point of ethanol, high boiling components having associated boiling points higher than the boiling point of ethanol, wherein the high boiling components include water;
      forming, within in the first distillation column, a polynary mixture with a plurality of azeotropes split from one another into separate distillation zones that are in fluid communication with one another within the first distillation column;
      removing, from the first distillation column, a stream of a first azeotrope of the plurality of azeotropes as an overhead stream that includes at least a portion of the low boiling components and a first portion of the high boiling components; and
      producing a first bottom stream from a second azeotrope of the plurality of azeotropes from the first distillation column;
   a water removal process including:

receiving a second feed stream including ethanol and high boiling components that include water, the second feed stream including at least a portion of the first bottom stream; and removing substantially all of the water from the second feed stream to produce an anhydrous stream; and a high boilers removal process including:

receiving in a second distillation column, a third feed stream including ethanol and high boiling components including a second portion of the high boiling components and water, the third feed stream being at least a portion of the anhydrous stream;

removing at least a portion of the high boiling components of the third feed stream from the third feed stream via a bottom stream of the second distillation column; and producing an overhead stream from the second distillation column, wherein the overhead stream of the second distillation column consists of a high-grade ethanol product that comprises fewer impurities than fuel grade ethanol.

2. The method of claim 1, wherein the first feed stream includes carbon dioxide, further comprising removing at least a portion of the carbon dioxide from the first feed stream prior to removing the portion of the low boiling components via the first distillation column.

3. The method of claim 1, wherein the first feed stream includes acetal, wherein the low boilers removal process further includes removing at least a portion of the acetal from the first feed stream via the overhead stream of the first distillation column.

4. The method of claim 1, wherein removing substantially all of the water from the second feed stream to produce an anhydrous stream includes:

generating a vaporous stream from the second feed stream via a stripper column; and contacting at least a portion of the vaporous stream with a membrane.

5. The method of claim 1, wherein removing substantially all of the water from the second feed stream to produce an anhydrous stream includes:

generating a vaporous stream from the second feed stream via a vaporizer; and contacting at least a portion of the vaporous stream with a molecular sieve unit.

6. The method of claim 1, wherein the bottom stream of the second distillation column includes a fuel-grade ethanol product.

7. The method of claim 1, wherein removing the portion of the low boiling components includes venting the portion of the low boiling components.

8. The method of claim 1, wherein the first feed stream includes at least a portion of a regen feed stream or at least a portion of a 190P feed stream.

9. The method of claim 1, wherein the second feed stream further includes at least a portion of a 190P feed stream.

10. The method of claim 1, further comprising:

receiving a third feed stream including ethanol and high boiling components that include water; and combining the third feed stream with the second feed stream to produce the anhydrous stream.

11. An ethanol production method comprising:

a low boilers removal process including:

receiving at a first distillation column at least one feed stream including ethanol, low boiling components having associated boiling points lower than a boiling point of ethanol, and high boiling components having associated boiling points higher than the boiling point of ethanol, wherein the high boiling components include water;

forming a polynary mixture with a plurality of azeotropes split into separate distillation segments that are in fluid communication with one another within the first distillation column;

removing a stream as an overhead stream from the first distillation column that includes at least a portion of the low boiling components and a first portion of the high boiling components; and a water removal process including:

generating a vaporous stream from the at least one feed stream via the first distillation column;

removing substantially all of the water from the vaporous stream via one or more membranes to produce an anhydrous stream including ethanol and high boiling components including water; and a high boilers removal process including:

receiving the anhydrous stream;

removing at least a portion of the high boiling components of the anhydrous stream from the anhydrous stream via a bottom stream of a second distillation column; and producing an overhead stream from the second distillation column, wherein the overhead stream consists of a high-grade ethanol product that comprises fewer impurities than fuel grade ethanol.

12. The method of claim 11, further comprising removing at least a portion of carbon dioxide contained in the at least one feed stream from the at least one feed stream prior to receiving the at least one feed stream at the first distillation column.

13. The method of claim 11, wherein the at least one feed stream includes two or more separate feed streams, each separate feed stream including ethanol, low boiling components, and high boiling components that include water.

14. The method of claim 11, wherein removing the at least the portion of the low boiling components includes venting the at least the portion of the low boiling.

15. An ethanol production method comprising:

a low boilers removal process including:

receiving at a first distillation column, a first feed stream including ethanol, low boiling components having associated boiling points lower than a boiling point of ethanol, and, high boiling components having associated boiling points higher than the boiling point of ethanol, wherein the high boiling components include water;

forming distillation zones in the first distillation column that each include a different polynary azeotrope of the low boiling components that are in fluid communication with at least one other polynary azeotrope in the first distillation column;

removing a stream within one distillation zone as an overhead stream from the first distillation column that includes at least a portion of the low boiling components and a first portion of the high boiling components; and producing a first bottom stream from the first distillation column;

a water removal process including:

receiving a second feed stream, the second feed stream including at least a portion of the first bottom stream; and removing at least a portion of the water from the second feed stream to produce a dehydrated stream; and a high boilers removal process including:
- receiving in a second distillation column, a third feed stream including ethanol and high boiling components including a second portion of the high boiling components and water, the third feed stream being at least a portion of the dehydrated stream;
- removing at least a portion of the high boiling components of the third feed stream from the third feed stream via a bottom stream of the second distillation column; and
- producing an overhead stream from the second distillation column, wherein the overhead stream of the second distillation column consists of a high-grade ethanol product that comprises fewer impurities than fuel grade ethanol.

* * * * *

UNITED STATES PATENT AND TRADEMARK OFFICE
CERTIFICATE OF CORRECTION

PATENT NO. : 11,697,630 B2
APPLICATION NO. : 17/398702
DATED : July 11, 2023
INVENTOR(S) : Virginia Andrade et al.

It is certified that error appears in the above-identified patent and that said Letters Patent is hereby corrected as shown below:

On the Title Page

Inventor Name item (72) reading "Zhou Jin Ming" should be changed to --Jin Ming Zhou--.

Signed and Sealed this
Second Day of January, 2024

Katherine Kelly Vidal
*Director of the United States Patent and Trademark Office*